United States Patent
Beach et al.

(10) Patent No.: US 8,500,794 B2
(45) Date of Patent: Aug. 6, 2013

(54) FLEXIBLE STENT

(75) Inventors: Bradley Beach, Belmar, NJ (US); Janet Burpee, Fairhaven, NJ (US)

(73) Assignee: Flexible Stenting Solutions, Inc., Eatontown, NJ (US)

( * ) Notice: Subject to any disclaimer, the term of this patent is extended or adjusted under 35 U.S.C. 154(b) by 48 days.

(21) Appl. No.: 13/161,980

(22) Filed: Jun. 16, 2011

(65) Prior Publication Data

US 2011/0245910 A1    Oct. 6, 2011

Related U.S. Application Data (62) Division of application No. 12/183,452, filed on Jul. 31, 2008, now Pat. No. 7,988,723.

(60) Provisional application No. 61/070,598, filed on Mar. 24, 2008, provisional application No. 60/963,083, filed on Aug. 2, 2007.

(51) Int. Cl.
*A61F 2/06*    (2006.01)

(52) U.S. Cl.
USPC ......................... 623/1.22; 623/1.15

(58) Field of Classification Search
USPC .............................. 623/1.15, 1.22
See application file for complete search history.

(56) References Cited

U.S. PATENT DOCUMENTS

| | | | |
|---|---|---|---|
| 4,307,723 A | 12/1981 | Finney | |
| 4,425,908 A | 1/1984 | Simon | |
| 4,432,132 A | 2/1984 | Kinsbron et al. | |
| 4,665,906 A | 5/1987 | Jervis | |
| 4,739,762 A | 4/1988 | Palmaz | |
| 4,740,207 A | 4/1988 | Kreamer | |
| 4,762,128 A | 8/1988 | Rosenbluth | |
| 4,776,337 A | 10/1988 | Palmaz | |
| 5,104,404 A | 4/1992 | Wolff | |
| 5,133,732 A | 7/1992 | Wiktor | |
| 5,190,546 A | 3/1993 | Jervis | |
| 5,197,978 A | 3/1993 | Hess | |
| 5,266,073 A | 11/1993 | Wall | |
| 5,275,622 A | 1/1994 | Lazarus et al. | |

(Continued)

FOREIGN PATENT DOCUMENTS

| EP | 0916317 A1 | 5/1999 |
|---|---|---|
| EP | 0941716 A2 | 9/1999 |

(Continued)

OTHER PUBLICATIONS

Pride et al., Endovascular Problem Solving with Intravascular Stents, AJNR Am. J. Neuroradiol., Mar. 2000, 21:532-540.

(Continued)

*Primary Examiner* — Thomas J Sweet
*Assistant Examiner* — Seema Mathew
(74) *Attorney, Agent, or Firm* — Porzio, Bromberg & Newman, P.C.

(57) ABSTRACT

The stent of the present invention combines a helical strut band interconnected by coil elements. This structure provides a combination of attributes that are desirable in a stent, such as, for example, substantial flexibility, stability in supporting a vessel lumen, cell size and radial strength. The structure of the stent of the present invention provides a predetermined geometric relationship between the helical strut band and interconnected coil elements in order to maintain connectivity at any diameter size state of the stent.

10 Claims, 10 Drawing Sheets

U.S. PATENT DOCUMENTS

| | | | |
|---|---|---|---|
| 5,292,321 A | 3/1994 | Lee | |
| 5,383,892 A | 1/1995 | Cardon et al. | |
| 5,395,390 A | 3/1995 | Simon et al. | |
| 5,449,373 A | 9/1995 | Pinchasik et al. | |
| 5,486,183 A | 1/1996 | Middleman et al. | |
| 5,507,767 A | 4/1996 | Maeda et al. | |
| 5,540,701 A | 7/1996 | Sharkey et al. | |
| 5,545,210 A | 8/1996 | Hess et al. | |
| 5,569,295 A | 10/1996 | Lam | |
| 5,591,197 A | 1/1997 | Orth et al. | |
| 5,591,198 A | 1/1997 | Boyle et al. | |
| 5,591,226 A | 1/1997 | Trerotola et al. | |
| 5,597,378 A | 1/1997 | Jervis | |
| 5,649,949 A | 7/1997 | Wallace et al. | |
| 5,662,703 A | 9/1997 | Yurek et al. | |
| 5,669,932 A | 9/1997 | Fischell et al. | |
| 5,693,085 A | 12/1997 | Buirge et al. | |
| 5,697,971 A | 12/1997 | Fischell et al. | |
| 5,716,396 A | 2/1998 | Williams, Jr. | |
| 5,718,713 A | 2/1998 | Frantzen | |
| 5,741,327 A | 4/1998 | Frantzen | |
| 5,749,919 A | 5/1998 | Blanc | |
| 5,755,781 A | 5/1998 | Jayaraman | |
| 5,776,142 A | 7/1998 | Gunderson | |
| 5,782,838 A | 7/1998 | Beyar et al. | |
| 5,800,456 A | 9/1998 | Maeda et al. | |
| 5,807,404 A | 9/1998 | Richter | |
| 5,810,872 A | 9/1998 | Kanesaka et al. | |
| 5,824,041 A | 10/1998 | Lenker et al. | |
| 5,836,964 A | 11/1998 | Richter et al. | |
| 5,843,120 A | 12/1998 | Israel et al. | |
| 5,843,175 A | 12/1998 | Frantzen | |
| 5,876,432 A | 3/1999 | Lau et al. | |
| 5,876,434 A | 3/1999 | Flomenblit et al. | |
| 5,891,192 A | 4/1999 | Murayama et al. | |
| 5,911,754 A | 6/1999 | Kanesaka et al. | |
| 5,913,895 A | 6/1999 | Burpee et al. | |
| 5,913,897 A | 6/1999 | Corso, Jr. et al. | |
| 5,919,225 A | 7/1999 | Lau et al. | |
| 5,925,061 A | 7/1999 | Ogi et al. | |
| 5,954,743 A | 9/1999 | Jang | |
| 5,961,548 A | 10/1999 | Shmulewitz | |
| 5,976,153 A | 11/1999 | Fischell et al. | |
| 5,989,280 A | 11/1999 | Euteneuer et al. | |
| 5,997,563 A | 12/1999 | Kretzers | |
| 6,004,330 A | 12/1999 | Middleman et al. | |
| 6,010,530 A | 1/2000 | Goicoechea | |
| 6,013,854 A | 1/2000 | Moriuchi | |
| 6,015,429 A | 1/2000 | Lau et al. | |
| 6,017,365 A | 1/2000 | Von Oepen | |
| 6,022,374 A | 2/2000 | Imran | |
| 6,039,756 A | 3/2000 | Jang | |
| 6,042,597 A | 3/2000 | Kveen et al. | |
| 6,042,606 A | 3/2000 | Frantzen | |
| 6,051,021 A | 4/2000 | Frid | |
| 6,059,813 A | 5/2000 | Vrba et al. | |
| 6,071,308 A | 6/2000 | Ballou et al. | |
| 6,077,296 A | 6/2000 | Shokoohi et al. | |
| 6,106,548 A | 8/2000 | Roubin et al. | |
| 6,117,165 A | 9/2000 | Becker | |
| 6,142,987 A | 11/2000 | Tsugita | |
| 6,156,062 A | 12/2000 | McGuinness | |
| 6,165,210 A | 12/2000 | Lau et al. | |
| 6,165,213 A | 12/2000 | Goicoechea et al. | |
| 6,168,621 B1 | 1/2001 | Vrba | |
| 6,190,403 B1 | 2/2001 | Fischell et al. | |
| 6,190,406 B1 | 2/2001 | Duerig et al. | |
| 6,193,744 B1 | 2/2001 | Ehr et al. | |
| 6,221,081 B1 | 4/2001 | Mikus et al. | |
| 6,231,598 B1 | 5/2001 | Berry et al. | |
| 6,241,757 B1 | 6/2001 | An et al. | |
| 6,241,762 B1 | 6/2001 | Shanley | |
| 6,251,132 B1 | 6/2001 | Ravenscroft et al. | |
| 6,251,134 B1 | 6/2001 | Alt et al. | |
| 6,254,609 B1 | 7/2001 | Vrba et al. | |
| 6,264,690 B1 | 7/2001 | Von Oepen | |
| 6,287,333 B1 | 9/2001 | Appling et al. | |
| 6,293,966 B1 | 9/2001 | Frantzen | |
| 6,306,141 B1 | 10/2001 | Jervis | |
| 6,334,871 B1 | 1/2002 | Dor et al. | |
| 6,340,367 B1 | 1/2002 | Stinson et al. | |
| 6,342,066 B1 | 1/2002 | Toro et al. | |
| 6,348,065 B1 | 2/2002 | Brown et al. | |
| 6,352,552 B1 | 3/2002 | Levinson et al. | |
| 6,355,059 B1 | 3/2002 | Richter et al. | |
| 6,369,355 B1 | 4/2002 | Saunders | |
| 6,375,676 B1 | 4/2002 | Cox | |
| 6,402,777 B1 | 6/2002 | Globerman et al. | |
| 6,409,752 B1 | 6/2002 | Boatman et al. | |
| 6,409,755 B1 | 6/2002 | Vrba | |
| 6,416,543 B1 | 7/2002 | Hilaire et al. | |
| 6,423,091 B1 | 7/2002 | Hojeibane | |
| 6,432,132 B1 | 8/2002 | Cottone et al. | |
| 6,464,720 B2 | 10/2002 | Boatman et al. | |
| 6,485,507 B1 | 11/2002 | Walak et al. | |
| 6,488,703 B1 * | 12/2002 | Kveen et al. | 623/1.15 |
| 6,492,615 B1 | 12/2002 | Flanagan | |
| 6,503,270 B1 | 1/2003 | Richter et al. | |
| 6,506,211 B1 | 1/2003 | Skubitz et al. | |
| 6,517,567 B2 | 2/2003 | Bass, Jr. et al. | |
| 6,517,569 B2 | 2/2003 | Mikus et al. | |
| 6,532,380 B1 | 3/2003 | Close et al. | |
| 6,533,807 B2 | 3/2003 | Wolinsky et al. | |
| 6,544,278 B1 | 4/2003 | Vrba et al. | |
| 6,551,351 B2 | 4/2003 | Smith et al. | |
| 6,562,067 B2 | 5/2003 | Mathis | |
| 6,562,898 B2 | 5/2003 | Masumoto | |
| 6,565,595 B1 | 5/2003 | DiCaprio et al. | |
| 6,579,308 B1 | 6/2003 | Jansen et al. | |
| 6,585,753 B2 | 7/2003 | Eder et al. | |
| 6,585,758 B1 | 7/2003 | Chouinard et al. | |
| 6,599,314 B2 | 7/2003 | Mathis | |
| 6,602,281 B1 | 8/2003 | Klein | |
| 6,605,111 B2 | 8/2003 | Bose et al. | |
| 6,607,552 B1 | 8/2003 | Hanson | |
| 6,612,012 B2 | 9/2003 | Mitelberg et al. | |
| 6,613,077 B2 | 9/2003 | Gilligan et al. | |
| 6,616,666 B1 | 9/2003 | Michelson | |
| 6,663,664 B1 | 12/2003 | Pacetti | |
| 6,666,882 B1 | 12/2003 | Bose et al. | |
| 6,669,721 B1 | 12/2003 | Bose et al. | |
| 6,676,683 B1 | 1/2004 | Addis | |
| 6,676,696 B1 | 1/2004 | Marotta et al. | |
| 6,682,554 B2 | 1/2004 | Oepen et al. | |
| 6,706,062 B2 | 3/2004 | Vardi et al. | |
| 6,730,117 B1 | 5/2004 | Tseng et al. | |
| 6,736,839 B2 | 5/2004 | Cummings | |
| 6,740,113 B2 | 5/2004 | Vrba | |
| 6,743,252 B1 | 6/2004 | Bates et al. | |
| 6,746,475 B1 | 6/2004 | Rivelli, Jr. | |
| 6,761,731 B2 | 7/2004 | Majercak | |
| 6,764,506 B2 | 7/2004 | Roubin et al. | |
| 6,805,898 B1 | 10/2004 | Wu et al. | |
| 6,821,292 B2 | 11/2004 | Pazienza et al. | |
| 6,830,638 B2 | 12/2004 | Boylan et al. | |
| 6,833,002 B2 | 12/2004 | Stack et al. | |
| 6,843,802 B1 | 1/2005 | Villalobos et al. | |
| 6,852,124 B2 | 2/2005 | Cox et al. | |
| 6,860,899 B1 | 3/2005 | Rivelli, Jr. | |
| 6,867,389 B2 | 3/2005 | Shapovalov et al. | |
| 6,878,162 B2 | 4/2005 | Bales et al. | |
| 6,896,696 B2 | 5/2005 | Doran et al. | |
| 6,899,727 B2 | 5/2005 | Armstrong et al. | |
| 6,899,730 B1 | 5/2005 | Rivelli, Jr. | |
| 6,913,617 B1 | 7/2005 | Reiss | |
| 6,916,617 B2 | 7/2005 | Gonsalves et al. | |
| 6,918,928 B2 | 7/2005 | Wolinsky et al. | |
| 6,923,828 B1 | 8/2005 | Wiktor | |
| 6,923,829 B2 | 8/2005 | Boyle et al. | |
| 6,942,682 B2 | 9/2005 | Vrba et al. | |
| 6,945,993 B2 | 9/2005 | Kveen et al. | |
| 6,949,120 B2 | 9/2005 | Kveen et al. | |
| 6,955,685 B2 | 10/2005 | Escamilla et al. | |
| 6,962,604 B2 | 11/2005 | Hijlkema | |
| 6,969,401 B1 | 11/2005 | Marotta et al. | |
| 6,969,402 B2 | 11/2005 | Bales et al. | |
| 6,981,985 B2 | 1/2006 | Brown et al. | |

| | | |
|---|---|---|
| 6,997,947 B2 | 2/2006 | Walak et al. |
| 7,004,960 B2 | 2/2006 | Daoud |
| 7,004,968 B2 | 2/2006 | Lootz et al. |
| 7,005,126 B1 | 2/2006 | Link, Jr. et al. |
| 7,018,403 B1 | 3/2006 | Pienknagura |
| 7,033,385 B2 | 4/2006 | Eder et al. |
| 7,033,386 B2 | 4/2006 | Richter et al. |
| 7,044,965 B1 | 5/2006 | Spielberg |
| 7,052,511 B2 | 5/2006 | Weldon et al. |
| 7,070,617 B2 | 7/2006 | Kula et al. |
| 7,077,854 B2 | 7/2006 | Khosravi |
| 7,081,132 B2 | 7/2006 | Cook et al. |
| 7,083,640 B2 | 8/2006 | Lombardi et al. |
| 7,090,695 B2 | 8/2006 | Solem et al. |
| 7,105,199 B2 | 9/2006 | Blinn et al. |
| 7,108,677 B2 | 9/2006 | Courtney et al. |
| 7,108,714 B1 | 9/2006 | Becker |
| 7,108,716 B2 | 9/2006 | Burnside et al. |
| 7,112,216 B2 * | 9/2006 | Gregorich .................. 623/1.15 |
| 7,118,592 B1 | 10/2006 | Dang et al. |
| 7,122,048 B2 | 10/2006 | DiMatteo et al. |
| 7,128,756 B2 | 10/2006 | Lowe et al. |
| 7,131,993 B2 | 11/2006 | Gregorich |
| 7,135,038 B1 | 11/2006 | Limon |
| 7,147,660 B2 | 12/2006 | Chobotov et al. |
| 7,163,552 B2 | 1/2007 | Diaz |
| 7,163,553 B2 | 1/2007 | Limon |
| 7,169,165 B2 | 1/2007 | Belef et al. |
| 7,169,170 B2 | 1/2007 | Widenhouse |
| 7,169,172 B2 | 1/2007 | Levine et al. |
| 7,169,174 B2 | 1/2007 | Fischell et al. |
| 7,169,175 B2 | 1/2007 | Cottone, Jr. et al. |
| 7,169,178 B1 | 1/2007 | Santos et al. |
| 7,175,650 B2 | 2/2007 | Ruetsch |
| 7,175,655 B1 | 2/2007 | Molaei |
| 7,179,289 B2 | 2/2007 | Shanley |
| 7,185,677 B2 | 3/2007 | Houston et al. |
| 7,186,263 B2 | 3/2007 | Golds et al. |
| 7,243,408 B2 | 7/2007 | Vietmeier |
| 7,294,146 B2 | 11/2007 | Chew et al. |
| 7,556,644 B2 | 7/2009 | Burpee et al. |
| 7,637,939 B2 * | 12/2009 | Tischler .................. 623/1.22 |
| 7,803,180 B2 * | 9/2010 | Burpee et al. .................. 623/1.15 |
| 7,935,142 B2 * | 5/2011 | Gregorich .................. 623/1.15 |
| 7,988,720 B2 * | 8/2011 | Brown et al. .................. 623/1.16 |
| 8,038,707 B2 * | 10/2011 | Bales et al. .................. 623/1.22 |
| 8,206,434 B2 * | 6/2012 | Lam .................. 623/1.22 |
| 8,226,705 B2 * | 7/2012 | Griswold .................. 623/1.22 |
| 2001/0056296 A1 | 12/2001 | Sugita et al. |
| 2002/0002400 A1 | 1/2002 | Drasler et al. |
| 2002/0042646 A1 | 4/2002 | Wall |
| 2002/0082682 A1 | 6/2002 | Barclay et al. |
| 2002/0143390 A1 | 10/2002 | Ishii |
| 2002/0165603 A1 | 11/2002 | Thornton et al. |
| 2002/0193868 A1 | 12/2002 | Mitelberg et al. |
| 2003/0050690 A1 | 3/2003 | Kveen et al. |
| 2003/0097172 A1 | 5/2003 | Shalev et al. |
| 2003/0114920 A1 | 6/2003 | Caro et al. |
| 2003/0149473 A1 | 8/2003 | Chouinard et al. |
| 2003/0149474 A1 | 8/2003 | Becker |
| 2003/0167084 A1 * | 9/2003 | Orlowski .................. 623/1.15 |
| 2003/0195609 A1 | 10/2003 | Berenstein et al. |
| 2003/0204244 A1 | 10/2003 | Stiger |
| 2003/0229390 A1 | 12/2003 | Ashton et al. |
| 2004/0002753 A1 | 1/2004 | Burgermeuster et al. |
| 2004/0034402 A1 * | 2/2004 | Bales et al. .................. 623/1.2 |
| 2004/0044401 A1 * | 3/2004 | Bales et al. .................. 623/1.22 |
| 2004/0088044 A1 | 5/2004 | Brown et al. |
| 2004/0122504 A1 | 6/2004 | Hogendijk |
| 2004/0147998 A1 | 7/2004 | Nolting |
| 2004/0149294 A1 | 8/2004 | Gianchandani et al. |
| 2004/0158306 A1 | 8/2004 | Mitelberg et al. |
| 2004/0172123 A1 | 9/2004 | Lootz et al. |
| 2004/0186556 A1 | 9/2004 | Hogendijk et al. |
| 2004/0193209 A1 | 9/2004 | Pavcnik et al. |
| 2004/0215325 A1 | 10/2004 | Penn et al. |
| 2004/0220663 A1 | 11/2004 | Rivelli, Jr. |
| 2004/0236401 A1 | 11/2004 | Shin et al. |
| 2004/0260384 A1 | 12/2004 | Allen |
| 2005/0015136 A1 | 1/2005 | Ikeuchi et al. |
| 2005/0033410 A1 | 2/2005 | Hogendijk et al. |
| 2005/0038495 A1 | 2/2005 | Greenan |
| 2005/0070992 A1 | 3/2005 | Bolduc et al. |
| 2005/0080479 A1 | 4/2005 | Feng et al. |
| 2005/0085842 A1 | 4/2005 | Eversull et al. |
| 2005/0085899 A1 | 4/2005 | Thornton |
| 2005/0090888 A1 | 4/2005 | Hines et al. |
| 2005/0096725 A1 | 5/2005 | Pomeranz et al. |
| 2005/0096727 A1 | 5/2005 | Allen et al. |
| 2005/0096732 A1 | 5/2005 | Marotta et al. |
| 2005/0113903 A1 | 5/2005 | Rosenthal et al. |
| 2005/0125025 A1 | 6/2005 | Rioux |
| 2005/0131426 A1 | 6/2005 | Moctezuma de la Barrera et al. |
| 2005/0131529 A1 | 6/2005 | Cragg |
| 2005/0131530 A1 | 6/2005 | Darack |
| 2005/0149164 A1 | 7/2005 | Rivelli, Jr. |
| 2005/0165469 A1 | 7/2005 | Hogendijk |
| 2005/0192661 A1 | 9/2005 | Griffen et al. |
| 2005/0246010 A1 | 11/2005 | Alexander et al. |
| 2006/0012922 A1 | 1/2006 | Shoji |
| 2006/0015171 A1 | 1/2006 | Armstrong |
| 2006/0020322 A1 | 1/2006 | Leynov et al. |
| 2006/0025849 A1 | 2/2006 | Kaplan et al. |
| 2006/0030932 A1 | 2/2006 | Kantor et al. |
| 2006/0030934 A1 | 2/2006 | Hogendijk et al. |
| 2006/0060266 A1 | 3/2006 | Bales et al. |
| 2006/0064154 A1 | 3/2006 | Bales et al. |
| 2006/0064158 A1 | 3/2006 | Bales et al. |
| 2006/0074480 A1 | 4/2006 | Bales et al. |
| 2006/0079955 A1 | 4/2006 | Brown |
| 2006/0142832 A1 | 6/2006 | Schmitt |
| 2006/0155312 A1 | 7/2006 | Levine et al. |
| 2006/0173490 A1 | 8/2006 | Lafontaine et al. |
| 2006/0184226 A1 | 8/2006 | Austin |
| 2006/0195137 A1 | 8/2006 | Sepetka et al. |
| 2006/0206002 A1 | 9/2006 | Frassica et al. |
| 2006/0247759 A1 | 11/2006 | Burpee et al. |
| 2006/0252624 A1 | 11/2006 | Kuribayashi et al. |
| 2007/0005126 A1 | 1/2007 | Tischler |
| 2007/0027522 A1 | 2/2007 | Chang et al. |
| 2007/0055365 A1 | 3/2007 | Greenberg et al. |
| 2007/0100423 A1 | 5/2007 | Acosta et al. |
| 2007/0129786 A1 | 6/2007 | Beach et al. |
| 2007/0156225 A1 | 7/2007 | George et al. |
| 2007/0198078 A1 | 8/2007 | Berra et al. |
| 2008/0132989 A1 | 6/2008 | Snow et al. |

FOREIGN PATENT DOCUMENTS

| | | |
|---|---|---|
| EP | 0950386 A2 | 10/1999 |
| EP | 0951877 A2 | 10/1999 |
| EP | 1452151 A2 | 9/2004 |
| EP | 2305175 A1 | 4/2011 |
| JP | 2002210021 A | 7/2002 |
| JP | 2002355315 A | 12/2002 |
| WO | 9603092 A1 | 2/1996 |
| WO | 9925272 A1 | 5/1999 |
| WO | 0016718 A1 | 3/2000 |
| WO | 0032136 A1 | 6/2000 |
| WO | 0032138 A1 | 6/2000 |
| WO | 0062711 A1 | 10/2000 |
| WO | 0126584 A1 | 4/2001 |
| WO | 0164133 A1 | 9/2001 |
| WO | 0193777 A2 | 12/2001 |
| WO | 02094127 A2 | 11/2002 |
| WO | 02094128 A2 | 11/2002 |
| WO | 03020102 A2 | 3/2003 |
| WO | 03022172 A2 | 3/2003 |
| WO | 2004110301 A2 | 12/2004 |
| WO | 2005063251 A1 | 7/2005 |
| WO | 2005076691 A2 | 8/2005 |
| WO | 2005120394 A2 | 12/2005 |
| WO | 2006047679 A1 | 5/2006 |

OTHER PUBLICATIONS

Lownie et al., Endovascular Therapy of a Large Vertebral Artery Aneurysm Using Stent and Coils, Can. J. Neurol. Sci., 2000, 27:162-165.

Wanke et al., Treatment of Wide-Necked Intracranial Aneurysms with a Self-Expanding Stent System: Initial Clinical Experience. ANJR Am. J. Neuroradiol., Jun./Jul. 2003, 24:1192-1199.

Rocha-Singh et al., Performance Goals of Endpoint Assessments for Clinical Trials of Feroropopliteal Bare Nitinol Stents in Patients with Symptomatic Peripheral Arterial Disease, Catheterization and Cardiovascular Interventions, 2007, 69:910-919.

* cited by examiner

FLEXIBLE STENT

CROSS-REFERENCE TO RELATED APPLICATION

This application is a divisional of U.S. patent application Ser. No. 12/183,452 filed Jul. 31, 2008, now U.S. Pat. No. 7,988,723 which claims the benefit of U.S. Provisional Patent Application No. 60/963,083 filed Aug. 2, 2007 and U.S. Provisional Patent Application No. 61/070,598 filed Mar. 24, 2008 the entireties of are hereby incorporated by reference into this application.

BACKGROUND OF THE INVENTION

1. Field of the Invention

The present invention relates generally to expandable tubular structures capable of insertion into small spaces in living bodies and, more particularly, concerns a stent structure having a geometry which is capable of substantial and repeated flexing at points along its length without mechanical failures and with no substantial changes in its geometry.

2. Description of the Related Art

A stent is a tubular structure that, in a radially compressed or crimped state, may be inserted into a confined space in a living body, such as a duct, an artery or other vessel. After insertion, the stent may be expanded radially to enlarge the space in which it is located. Stents are typically characterized as balloon-expanding (BX) or self-expanding (SX). A balloon-expanding stent requires a balloon, which is usually part of a delivery system, to expand the stent from within and to dilate the vessel. A self expanding stent is designed, through choice of material, geometry, or manufacturing techniques, to expand from the crimped state to an expanded state once it is released into the intended vessel. In certain situations higher forces than the expanding force of the self expanding stent are required to dilate a diseased vessel. In this case, a balloon or similar device might be employed to aid the expansion of a self expanding stent.

Stents are typically used in the treatment of vascular and non-vascular diseases. For instance, a crimped stent may be inserted into a clogged artery and then expanded to restore blood flow in the artery. Prior to release, the stent would typically be retained in its crimped state within a catheter and the like. Upon completion of the procedure, the stent is left inside the patient's artery in its expanded state. The health, and sometimes the life, of the patient depend upon the stent's ability to remain in its expanded state.

Many conventional stents are flexible in their crimped state in order to facilitate the delivery of the stent, for example within an artery. Few are flexible after being deployed and expanded. Yet, after deployment, in certain applications, a stent may be subjected to substantial flexing or bending, axial compressions and repeated displacements at points along its length, for example, when stenting the superficial femoral artery. This can produce severe strain and fatigue, resulting in failure of the stent.

A similar problem exists with respect to stent-like structures. An example would be a stent-like structure used with other components in a catheter-based valve delivery system. Such a stent-like structure holds a valve which is placed in a vessel.

SUMMARY OF THE INVENTION

The stent of the present invention combines a helical strut member or band interconnected by coil elements. This structure provides a combination of attributes that are desirable in a stent, such as, for example, substantial flexibility, stability in supporting a vessel lumen, cell size and radial strength. However, the addition of the coil elements interconnecting the helical strut band complicates changing the diameter state of the stent. Typically a stent structure must be able to change the size of the diameter of the stent. For instance, a stent is usually delivered to a target lesion site in an artery while in a small diameter size state, then expanded to a larger diameter size state while inside the artery at the target lesion site. The structure of the stent of the present invention provides a predetermined geometric relationship between the helical strut band and interconnected coil elements in order to maintain connectivity at any diameter size state of the stent.

The stent of the present invention is a self expanding stent made from superelastic nitinol. Stents of this type are manufactured to have a specific structure in the fully expanded or unconstrained state. Additionally a stent of this type must be able to be radially compressed to a smaller diameter, which is sometimes referred to as the crimped diameter. Radially compressing a stent to a smaller diameter is sometimes referred to as crimping the stent. The difference in diameter of a self expanding stent between the fully expanded or unconstrained diameter and the crimped diameter can be large. It is not unusual for the fully expanded diameter to be 3 to 4 times larger than the crimped diameter. A self expanding stent is designed, through choice of material, geometry, and manufacturing techniques, to expand from the crimped diameter to an expanded diameter once it is released into the intended vessel.

The stent of the present invention comprises a helical strut band helically wound about an axis of the strut. The helical strut band comprises a wave pattern of strut elements having a plurality of peaks on either side of the wave pattern. A plurality of coil elements are helically wound about an axis of the stent and progress in the same direction as the helical strut band. The coil elements are typically elongated where the length is much longer than the width. The coil elements interconnect at least some of the strut elements of a first winding to at least some of the strut elements of a second winding of the helical strut band at or near the peaks of the wave pattern. In the stent of the present invention, a geometric relationship triangle is constructed having a first side with a leg length $L_C$ being the effective length of the coil element between the interconnected peaks of a first and second winding of the helical strut band, a second side with a leg length being the circumferential distance between the peak of the first winding and the peak of the second winding interconnected by the coil element divided by the sine of an angle $A_s$ of the helical strut band from a longitudinal axis of the stent, a third side with a leg length being the longitudinal distance the helical strut band progresses in 1 circumference winding (Pl) minus the effective strut length $L_S$, a first angle of the first leg being 180 degrees minus the angle $A_s$, a second angle of the second leg being an angle $A_c$ the coil element generally progresses around the axis of the stent measured from the longitudinal axis and a third angle of the third leg being the angle $A_s$ minus the angle $A_c$, wherein a ratio of the first leg length $L_C$ to a length $L_S$ multiplied by the number of adjacent wave pattern of the strut elements forming the helical strut band, $N_S$ is greater than or equal to about 1. This value is defined as the coil-strut ratio and numerically is represented by coil-strut ratio=Lc/Ls*Ns.

BRIEF DESCRIPTION OF THE DRAWINGS

The foregoing description, as well as further objects, features, and advantages of the present invention will be understood more completely from the following detailed description of presently preferred, but nonetheless illustrative embodiments in accordance with the present invention, with reference being had to the accompanying drawings, in which.

DETAILED DESCRIPTION OF THE PREFERRED EMBODIMENTS

Reference will now be made in greater detail to a preferred embodiment of the invention, an example of which is illustrated in the accompanying drawings. Wherever possible, the same reference numerals will be used throughout the drawings and the description to refer to the same or like parts.

Figure 1:
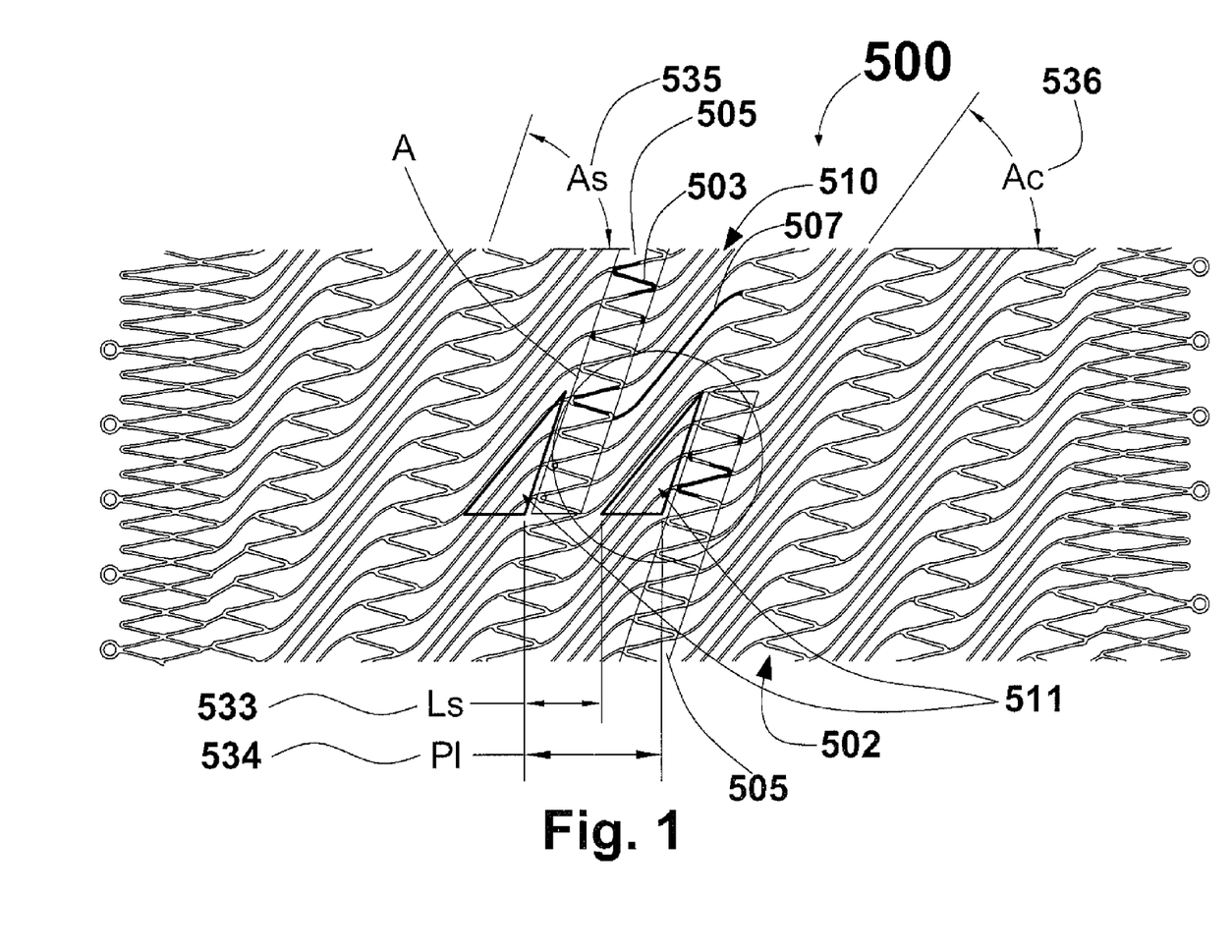
FIG. 1 is a plan view of a first embodiment of a stent in accordance with the present invention, the stent being shown in a partially expanded state.
Figure 2:
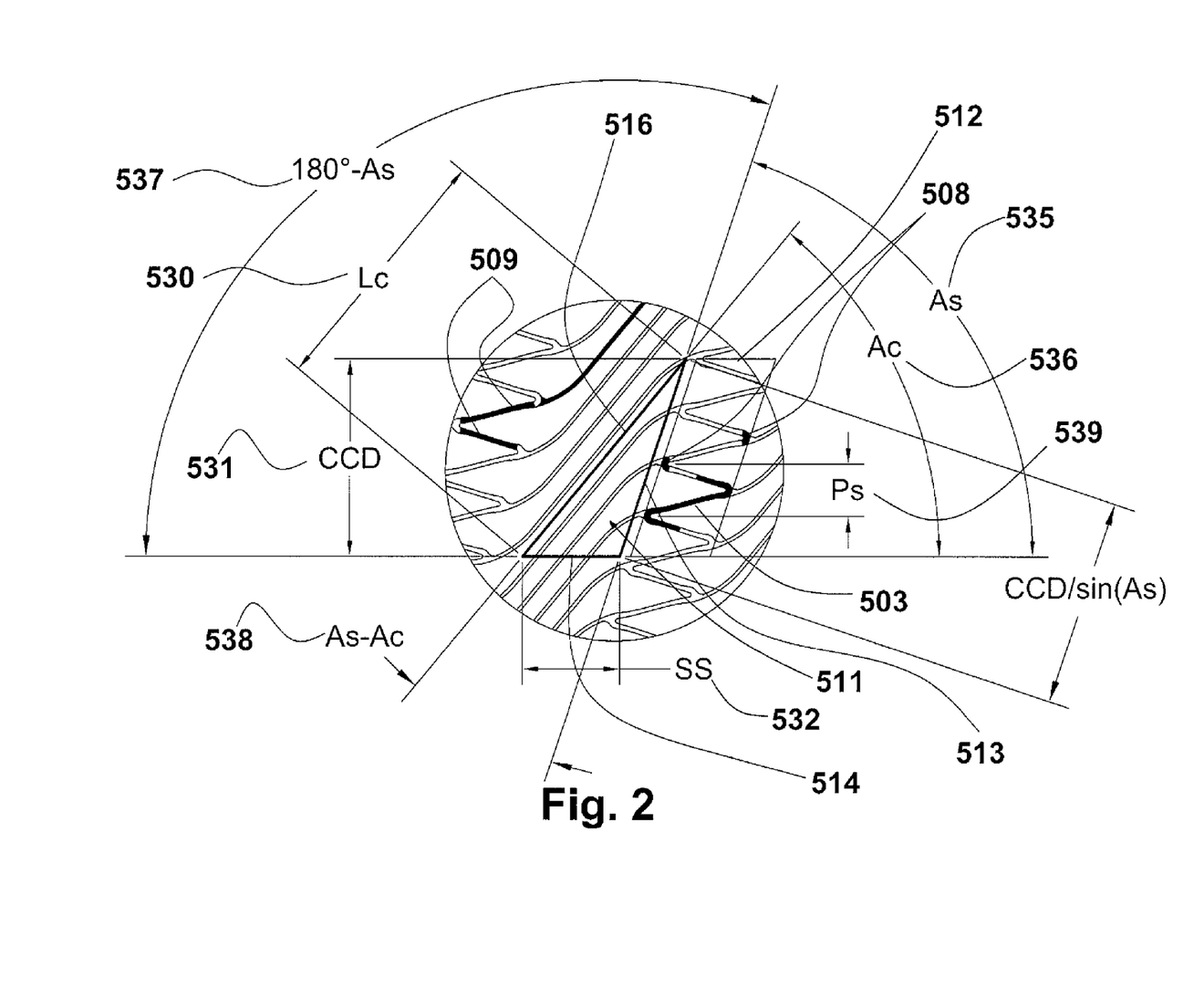
FIG. 2 is a detailed enlarged view of portion A shown in FIG. 1.

FIG. 1 with detail shown in FIG. 2 illustrates stent 500. FIG. 1 is a plan view of a first embodiment of stent 500 in accordance with the present invention shown in a partially expanded state. As used herein, the term "plan view" will be understood to describe an unwrapped plan view. This could be thought of as slicing open a tubular stent along a line parallel to its axis and laying it out flat. It should therefore be appreciated that, in the actual stent, the top edge of FIG. 1 will be joined to the lower edge. Stent 500 is comprised of helical strut band 502 interconnected by coil elements 507. Side-by-side coil elements 507 form coil band 510. Coil band 510 is formed as a double helix with helical strut band 502 and progresses from one end of the stent to the other. Helical strut band 502 comprises a wave pattern of strut elements 503 that have peaks 508 on either side of the wave pattern and legs 509 between peaks 508. Coil elements 507 interconnect strut elements 503 of helical strut band 502 through or near peaks 508. NSC portion 505 of helical strut band 502 is defined by the number of strut elements 503 (NSC) of helical strut band 502 between coil element 507 as helical strut band 502 progresses around stent 500. The number of strut elements 503 (NSC) in NSC portion 505 of helical strut band 502 is more than the number of strut elements 503 (N) in one circumference winding of helical strut band 502. The number of strut elements 503 (NSC) in NSC portion 505 is constant.

Figure 10:
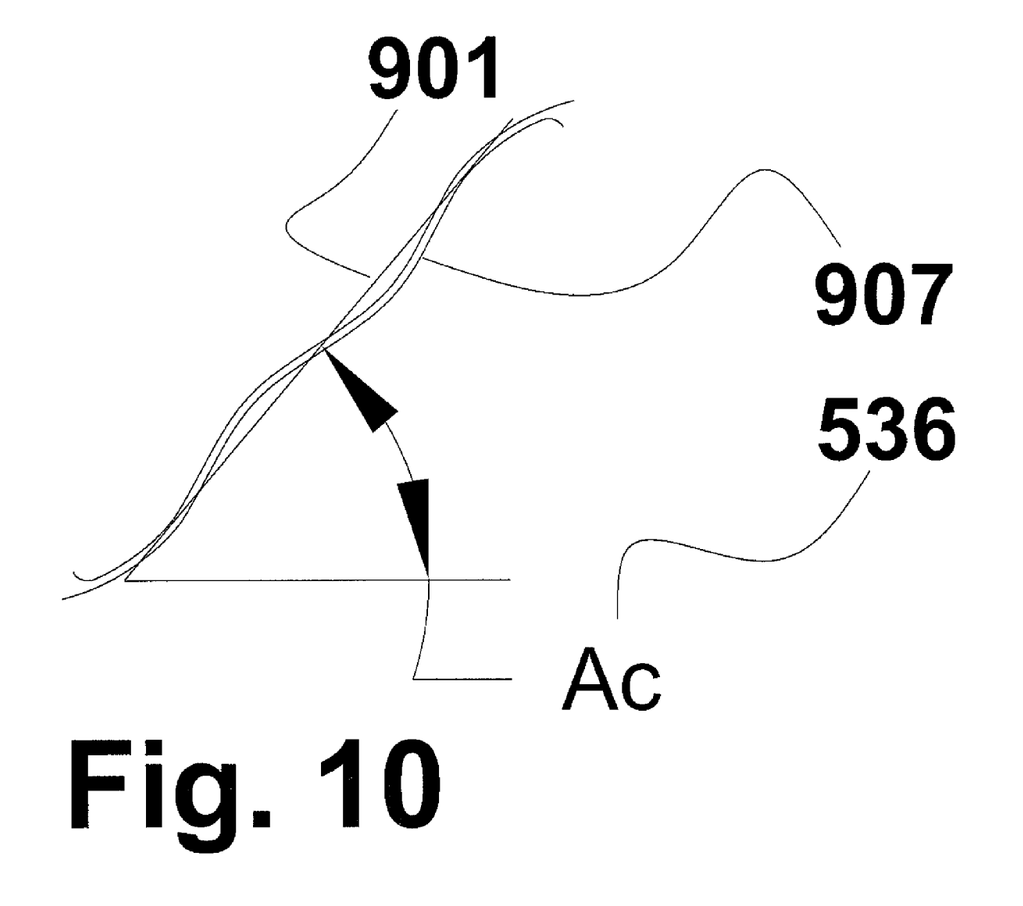
FIG. 10 is a schematic diagram of an alternate embodiment for a coil element of the stent.

In this embodiment, stent 500 has N=12.728 helical strut elements 503 in one circumference winding of helical strut band 502 and has NSC=16.5 helical strut elements 503 in NSC portion 505. CCDn portion 512 of NSC portion 505 of helical strut band 502 is defined by the number of strut elements 503 (CCDn) equal to NSC minus N. The number of strut elements 503 (CCDn) in CCDn portion 512 and the number of strut elements 503 (N) in one circumference winding of helical strut band 502 does not need to be constant at different diameter size states of stent 500. Stent 500 has CCDn=3.772 helical strut elements 503 in CCDn portion 512. Because this connectivity needs to be maintained at any diameter size state a geometric relationship between the helical strut band 502 and coil element 507 can be described by geometric relationship triangle 511. Geometric relationship triangle 511 has a first side 516 with a leg length equal to the effective length (Lc) 530 of coil element 507, a second side 513 with a leg length equal to circumferential coil distance (CCD) 531 of CCDn portion 512 of helical strut band 502 divided by the sine of an angle $A_s$ 535 of helical strut band 502 from the longitudinal axis of stent 500, a third side 514 with a leg length (SS) 532 equal to the longitudinal distance (Pl) 534 helical strut band 502 progresses in 1 circumference winding minus the effective strut length $L_S$ 533, a first angle 537 of first side 516 is equal to 180 degrees minus angle $A_s$ 535, a second angle 536 of second side 513 is equal to the angle $A_c$ 536 of coil element 507 from the longitudinal axis of stent 500 and a third angle 538 of third side 514 equal to angle $A_s$ 535 minus angle $A_c$ 536. If the circumferential strut distance ($P_s$) 539 of helical strut element 503 is the same for all helical strut elements 503 in CCDn portion 512, circumferential coil distance CCD 531 is equal to the number of helical strut elements 503 in the CCDn portion 512 multiplied by the circumferential strut distance ($P_s$) 539. The distances in any figure that shows a flat pattern view of a stent represent distances on the surface of the stent, for example vertical distances are circumferential distances and angled distances are helical distances. First side 516 of geometric relationship triangle 511 is drawn parallel to the linear portion of coil element 507 such that the coil angle Ac 536 is equal to the angle of the linear portion of coil element 507. If coil element 507 does not have a substantially linear portion, but progresses about the stent in a helical manner, an equivalent coil angle 536 could be used to construct the geometric relationship triangle 511. For instance if coil element 507 is a wavy coil element 907, as shown in FIG. 10, line 901 could be drawn fitted through the curves of the wavy coil element 907 and line 901 can be used to define coil angle 536.

Figure 3:
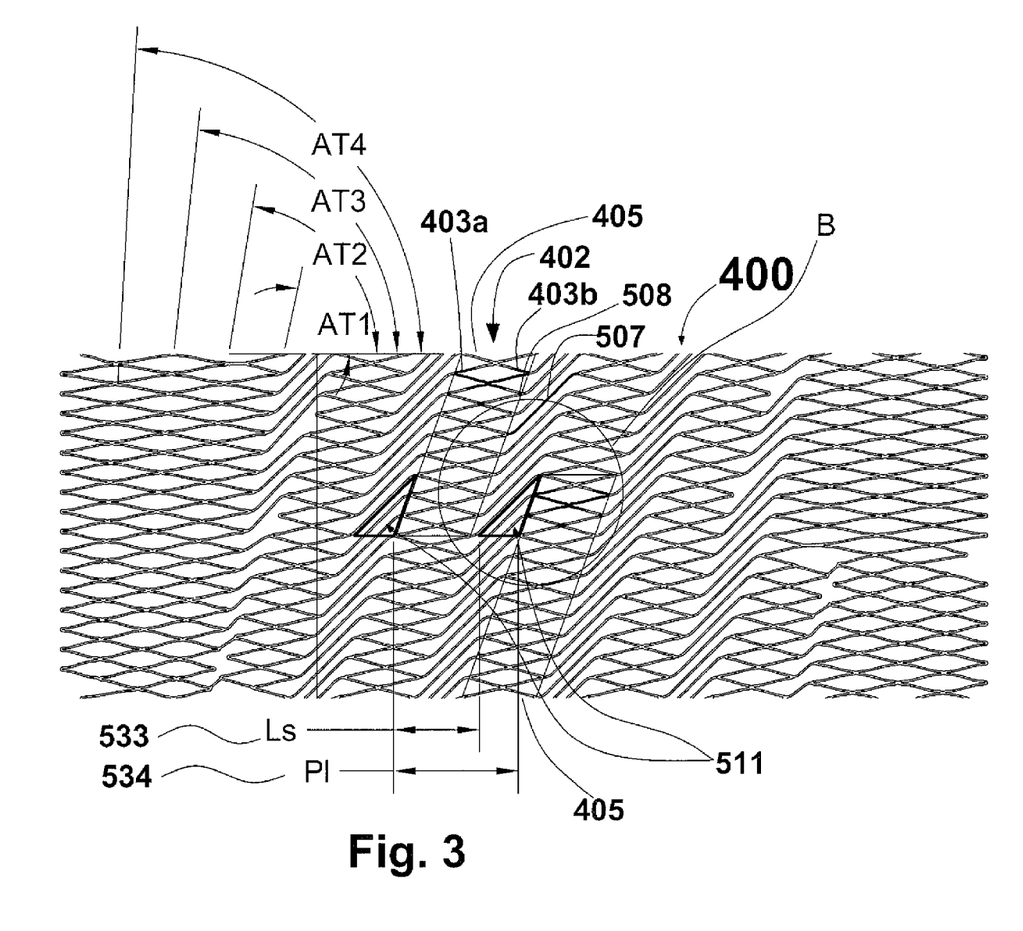
FIG. 3 is a plan view of an alternate embodiment of the stent.
Figure 4:
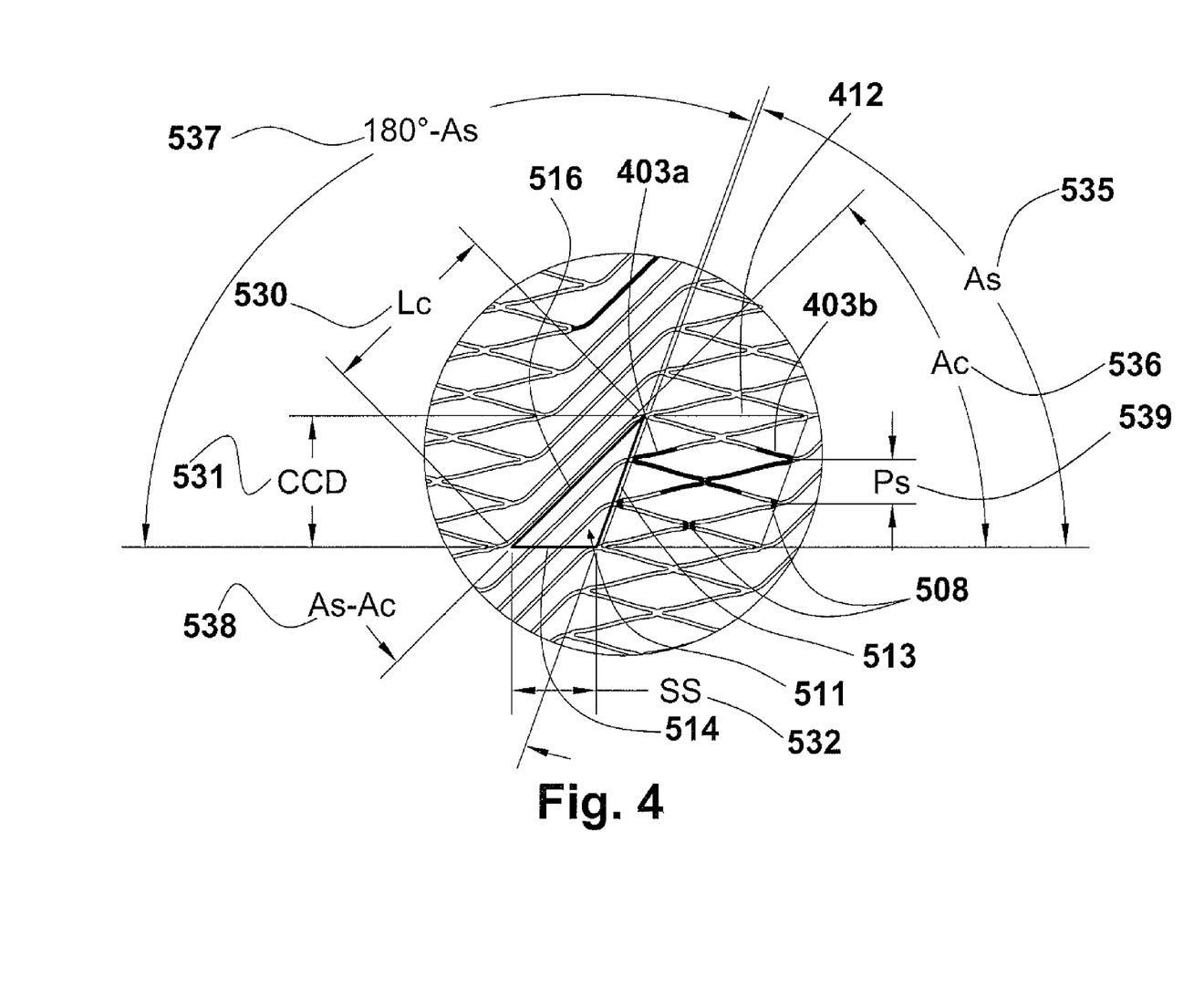
FIG. 4 is an enlarged detailed view of portion B shown in FIG. 3.

Stent 400 shown in FIGS. 3 and 4 is similar to stent 500 in that it is comprised of helical strut band 402 interconnected by coil elements 507. Stent 400 is different in that helical strut band 402 is comprised of two adjacent wave patterns of strut elements 403a and 403b that have peaks 508 on either side of the wave pattern. Strut element 403a being connected to strut element 403b. Similar to helical strut band 502, helical strut band 402 also has a NSC portion 405 and a CCDn portion 412. Helical strut band 402 can be defined as having a number Ns of wave patterns of strut elements equal to 2. Helical strut band 502 can be defined as having a number Ns of wave patterns of strut elements equal to 1. In an alternate embodiment, the stent of the present invention can have a helical strut band with a number Ns of wave patterns of strut elements equal to 3, which would be a triple strut band. In an alternate embodiment, the stent of the present invention could have a helical strut band with a number Ns of wave patterns of strut elements equal to any integer. Stents with helical strut bands having a number Ns of wave patterns of strut elements equal to or greater than 2 provide an advantage in that the helical strut band would form a closed cell structure with smaller cell size which is desired when there is additional risk of embolism. Stents with smaller cell sizes tend to trap plaque or other potential embolic debris better than stents with larger cell sizes.

Figure 9:
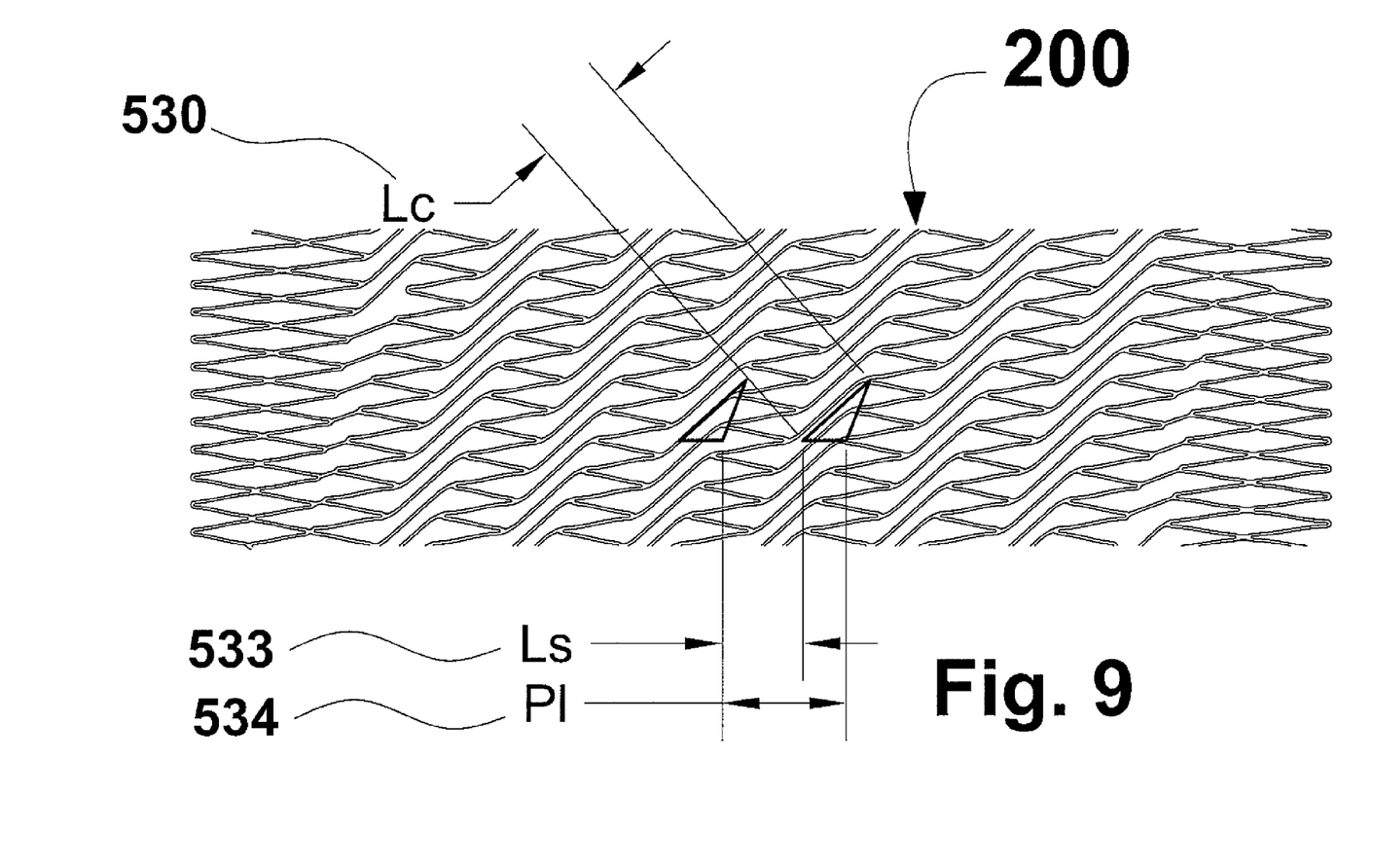
FIG. 9 is a plan view of an alternate embodiment of the stent.

Stent structures described provides the combination of attributes desirable in a stent when the coil-strut ratio, ratio of Lc to Ls multiplied by the number of wave patterns of strut elements Ns in the helical strut band (Lc multiplied by Ns divided by Ls), is greater than or equal to 1. For example the coil-strut ratio for stent 500 is 2.06 and for stent 400 is 2.02. Stent 200 shown in FIG. 9 has a similar structure to stent 500. The coil-strut ratio for stent 200 is about 1.11.

In order for the stent of the present invention to crimped to a smaller diameter, the geometry of the structure undergoes several changes. Because of the helical nature of the helical strut band, strut angle $A_s$ must get smaller as the stent diameter decreases. Because of the interconnectivity between a first winding of the helical strut band and a second winding of the helical strut band created by the coil element, the angle of the element $A_c$ must also get smaller, or become shallower, to accommodate the smaller strut angle $A_s$. If the angle of coil element $A_c$ can not become shallower or is difficult to become shallower as the stent crimps and stent angle $A_s$ gets smaller, the coil elements will tend to interfere with each other and prohibit crimping or require more force to crimp. The changing of the angle of the coil element during crimping is facilitated if the coil-strut ratio is greater than 1. Coil-strut ratios less than 1 tend to stiffen the coil element such that more force is required to bend the coil element to a shallower angle during the crimping process, which is not desirable.

Figure 5:
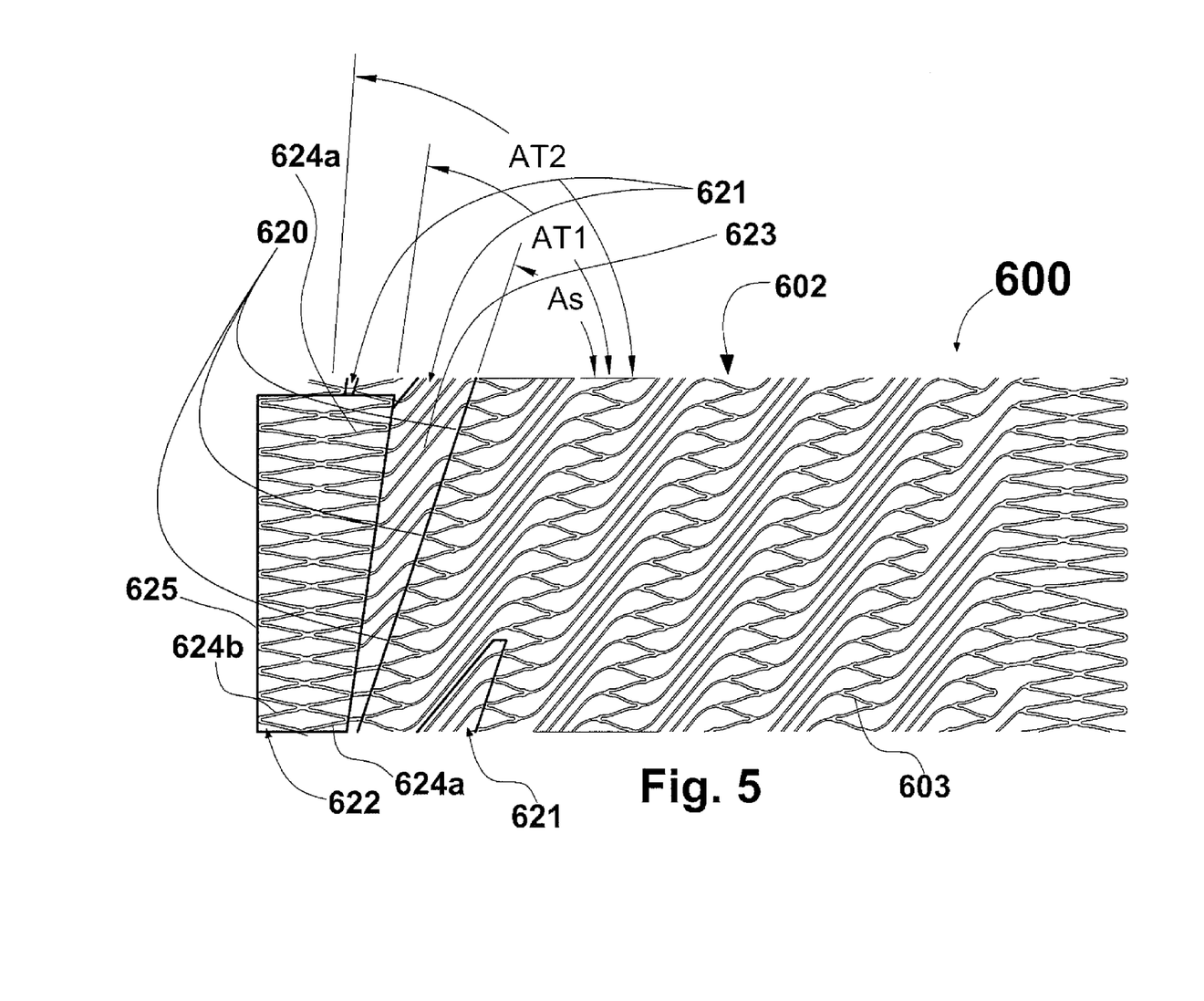
FIG. 5 is a plan view of an alternate embodiment of the stent.

Helical strut band 602 of stent 600, shown in FIG. 5, transitions to and continues as an end strut portion 622 where the angle of the winding AT1 of the wave pattern of strut elements 624a forming end strut portion 622 is larger than the angle of the helical strut band $A_s$. End strut portion 622 includes a second winding of the wave pattern of strut elements 624b where the angle AT2 of the second winding is larger than the angle of the first winding AT1. Strut elements 603 of helical strut band 602 are interconnected to strut elements 624a of the first winding of end strut portion 622 by a series of transitional coil elements 623 that define transition coil portion 621. All strut elements 624a of the first winding of end portion 622 are connected by coil elements 623 to the helical strut band 602. Peaks 620 of helical strut band 602 are not connected to end strut portion 622. Transitional coil portion 621 allows end strut portion 622 to have a substantially flat end 625. Helical strut band 402 of stent 400 transitions to and continues as an end portion where the angle of the first winding AT1 of the wave pattern of strut elements forming of the end portion is larger than the angle of the helical strut band As. The angle of the second winding AT2 is larger than AT1, and the angle of subsequent windings of the end portion are also increasing (i.e. AT1<AT2<AT3<AT4).

The accompanying definitions are described below.

(N)—Number of helical strut elements in one circumference winding of the helical strut member.

($A_s$)—Angle of helical strut band winding measured from the longitudinal axis of the stent.

($A_c$)—Effective angle of coil element measured from the longitudinal axis of the stent.

(Pl)—Longitudinal distance (pitch) the strut member progresses in 1 circumference winding. Equal to the circumference of the stent divided by the arctangent of $A_s$.

($P_s$)—Circumferential distance (pitch) between strut legs of a helical strut element of the helical strut band. Assuming the circumferential strut pitch is equal for all strut elements of the helical strut band, the circumferential strut pitch is equal to the circumference of the stent divided by N.

(NSC)—Number of strut elements of the strut band between a helical element as the strut member progresses (CCDn)—Number of strut elements of the strut band between interconnected strut elements, equal to NSC minus N (CCD)—Circumferential Coil Distance is the circumferential distance between interconnected strut elements, equal to the CCDn times the $P_s$ if the Ps is equal for all strut elements in the CCDn portion.

(Lc)—Effective length of the helical element as defined by the geometric relationship triangle described in table 1.

(SS)—Strut Separation as defined in the geometric relationship triangle described in table 1.

(Ls)—Effective Strut Length. Equal to Pl minus SS.

(Ns)—Number of adjacent wave patterns of the strut elements forming the helical strut band.

Coil-Strut ratio—Ratio of $L_C$ to a length $L_S$ multiplied by the number of adjacent wave pattern of the strut elements forming the helical strut band, $N_S$. Numerically equal to Lc/Ls*Ns.

Strut length-Strut Separation ratio—Ratio of the effective strut length (Ls) to the Strut Separation (SS), numerically equal to Ls/SS.

TABLE 1

|  | Leg Length | Angle |
| --- | --- | --- |
| Side 1 | Lc | 180° minus $A_s$ |
| Side 2 | CCD divided by sin($A_s$) | $A_c$ |
| Side 3 | SS | $A_s$ minus $A_c$ |

In one embodiment, the difference between the strut angle, $A_s$, and coil angle, $A_c$, is more than about 20 degrees. Because of the necessity of the coil angle to become shallower as the stent is crimped, if the coil angle and the strut angle in the expanded state are too close to each other there is increased difficulty in crimping the stent.

For the stent of the present invention the Strut length—Strut Separation ratio is a measure of the relative angle of the strut angle and coil angle. Stents with Strut length—Strut Separation ratios less than about 2.5 have improved crimping behavior. Stent attributes can further be improved if the angle of the strut member is between 55 degrees and 80 degrees and the coil angle is between 45 degrees and 60 degrees in the expanded state. Additionally, steeper coil angles $A_c$ in the expanded state make crimping the stent of the present invention more difficult. Coil angles of less than 60 degrees in the expanded state facilitate crimping the stent of the present invention.

For the stent of the present invention, in addition to the coil angle changing during crimping, the helical strut band rotates about the longitudinal axis of the stent to accommodate the connectivity between subsequent windings of helical strut bands during crimping resulting in more windings of the helical strut band along the length of the stent when the stent is crimped. For the stent of the present invention, the geometric relationship triangle can be used to approximate the expected amount of helical strut band rotation during crimping of the stent. If the geometric relationship triangle can be determined for a given diameter size state of the stent, the geometric relationship triangle can be approximated for any other size state based on the following assumptions; the effective coil length ($L_c$), effective strut length ($L_s$), and the longitudinal pitch of the helical strut band (Pl) are a constant for any diameter size state. Given the above assumptions and the geometric relationship triangles approximated in the expanded and crimped states, the amount the helical strut band rotates per winding of the helical strut band about the axis of the stent to accommodate the interconnected coil element during crimping can be approximated if the circumferential strut pitch ($P_s$) of the strut element of the helical strut band is assumed to be equal for all strut elements in the helical strut band. Considering that an increase of helical strut band windings along the length of the stent when the stent is crimped contributes to stent foreshortening it is advantageous for the stent of the present invention to have an approximated increase in the amount of helical strut band windings of less than about 30% when crimped, preferably less than about 26%. A 26% increase in helical strut band winding corresponds to about 20% foreshortening which is considered the maximum clinically useful amount of foreshortening (Serruys, Patrick, W., and Kutryk, Michael, J. B., Eds., *Handbook of CoronaryStents, Second Edition*, Martin Dunitz Ltd., London, 1998.) hereby incorporated by reference in its entirety into this application.

Figure 6:
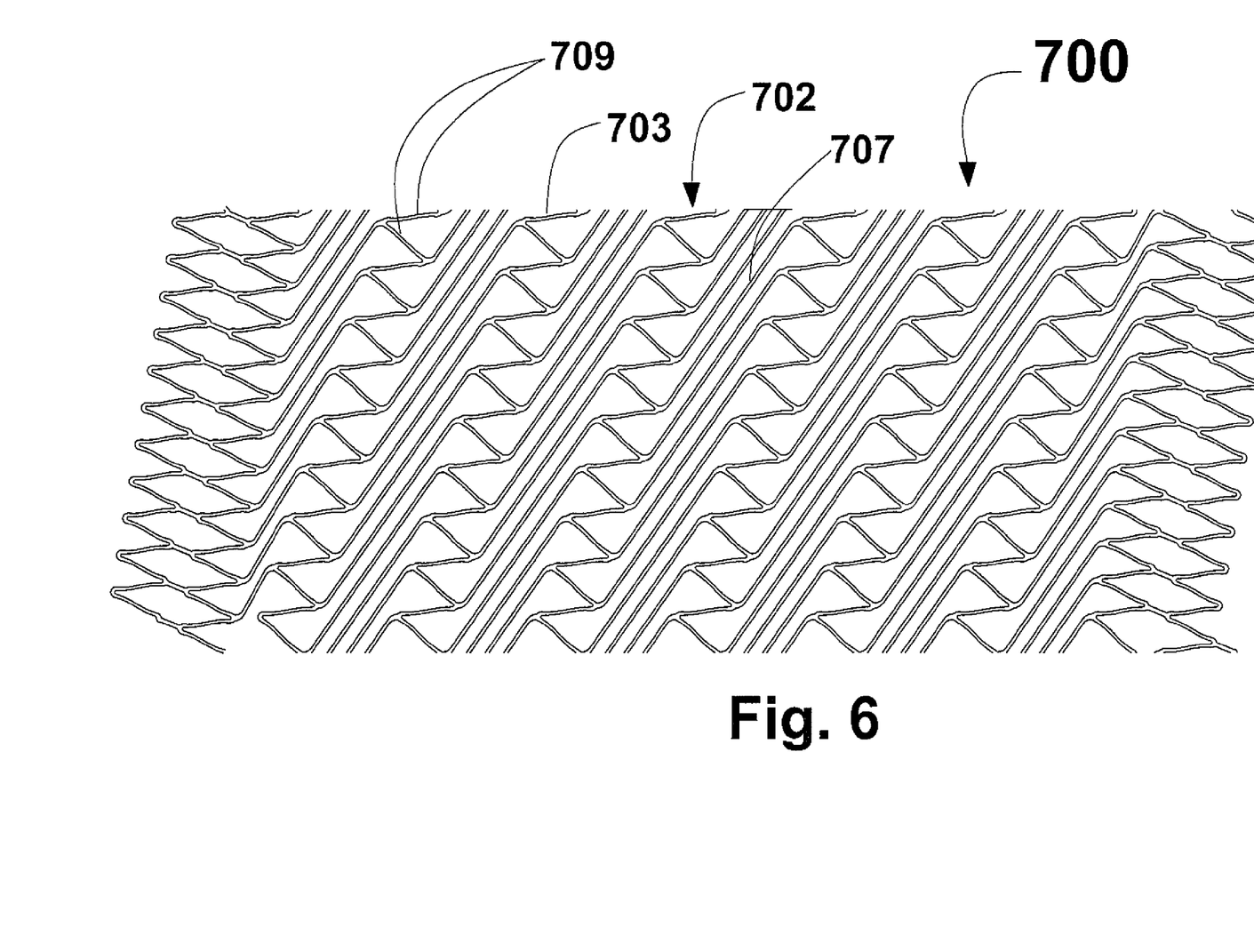
FIG. 6 is a plan view of an alternate embodiment of the stent.

FIG. 6 is a plan view of another embodiment of stent 700 in accordance with the teachings of the present invention. Helical strut band 702 progresses helically from one end of stent 700 to the other. Each strut element 703 is connected to a strut in a subsequent winding of helical strut band 702 by coil element 707. Strut element 703 includes leg portions 709. Each of leg portions 709 has an equal length.

Figure 7:
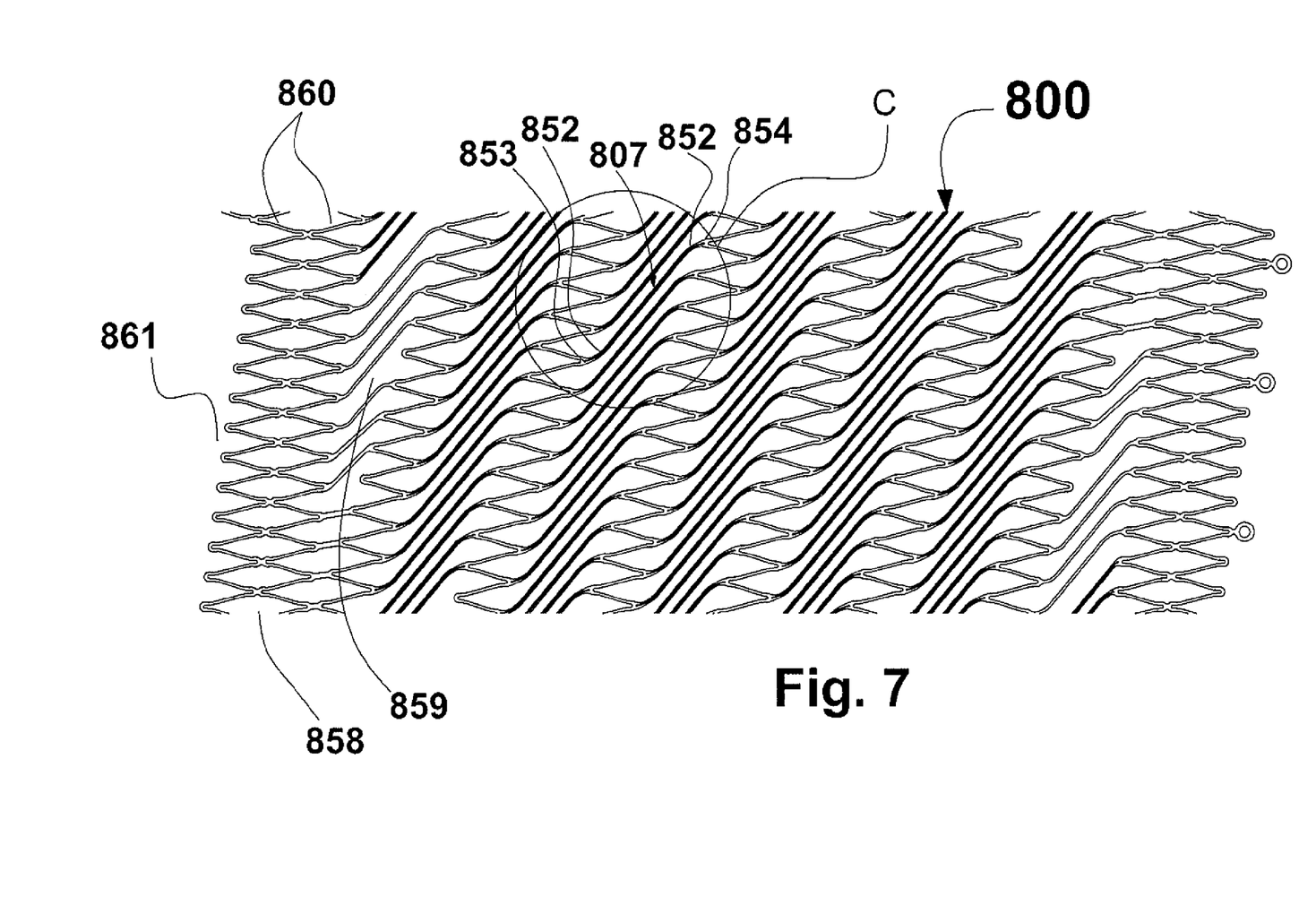
FIG. 7 is a plan view of an alternate embodiment of the stent.
Figure 8:
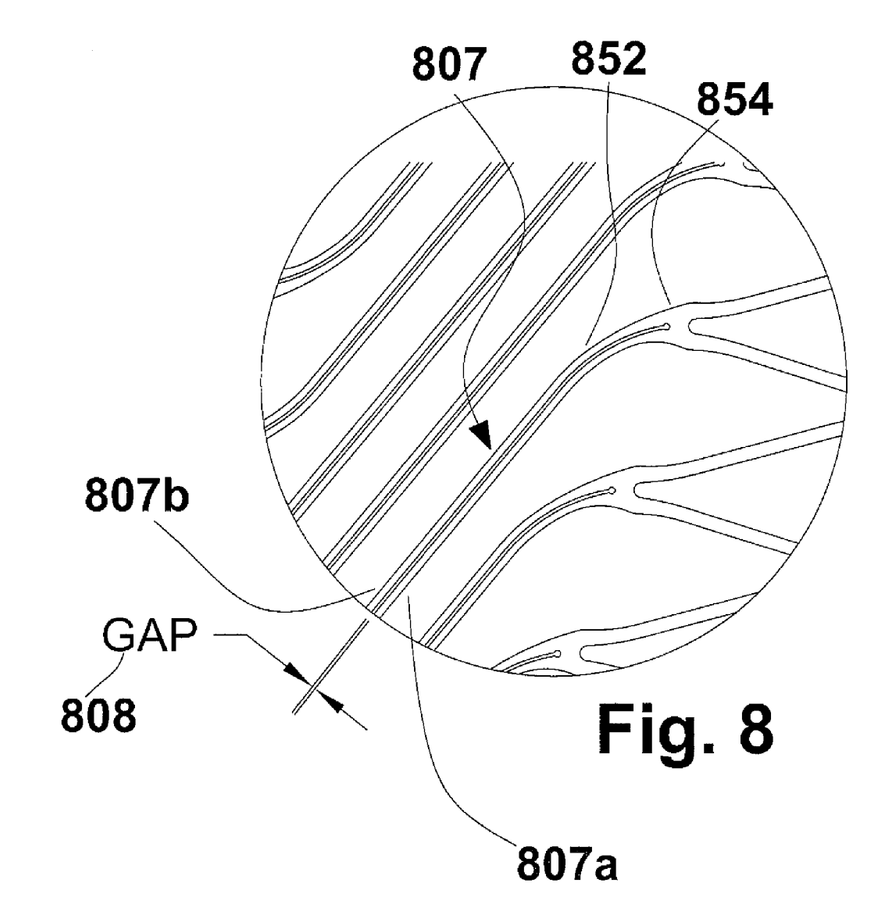
FIG. 8 is a detailed enlarged view of portion C shown in FIG. 7.

FIG. 7, with detail shown in FIG. 8, is a plan view of another embodiment of stent 800. In this embodiment, coil element 807 includes curved transition portion 852 at ends 853 and 854. Curved transition portion 852 connects to strut element 803.

Stent 800 includes transitional helical portions 859 and end strut portions 858 at either end 861 of stent 800. End strut portions 858 are formed of a pair of connected strut windings 860. Coil element 807 is comprised of two coil portions 807a and 807b which are separated by gap 808, as shown in FIG. 8. Gap 808 can have a size equal to zero where coil portions 807a and 807b are touching. Gap 808 terminates near ends 853 and 854. Gap 808 can terminate anywhere along the length of coil 807 or at multiple points along coil 807 such that the gap would have interruptions along coil 807.

Stents 400, 500, 600, 700 and 800 are made from a common material for self expanding stents, such as Nitinol nickel-titanium alloy (Ni/Ti), as is well known in the art.

The stents of the present invention may be placed within vessels using procedures well known in the art. The stents may be loaded into the proximal end of a catheter and advanced through the catheter and released at the desired site. Alternatively, the stents may be carried about the distal end of the catheter in a compressed state and released at the desired site. The stents may either be self-expanding or expanded by means such as an inflatable balloon segment of the catheter. After the stent(s) have been deposited at the desired intralumenal site, the catheter is withdrawn.

The stents of the present invention may be placed within body lumen such as vascular vessels or ducts of any mammal species including humans, without damaging the lumenal wall. For example, the stent can be placed within a lesion or an aneurysm for treating the aneurysm. In one embodiment, the flexible stent is placed in a super femoral artery upon insertion into the vessel. In a method of treating a diseased vessel or duct a catheter is guided to a target site of a diseased vessel or duct. The stent is advanced through the catheter to the target site. For example, the vessel can be a vascular vessel, femoropopliteal artery, tibial artery, carotid artery, iliac artery, renal artery, coronary artery, neurovascular artery or vein.

Stents of the present invention may be well suited to treating vessels in the human body that are exposed to significant biomechanical forces. Stents that are implanted in vessels in the human body that are exposed to significant biomechanical forces must pass rigorous fatigue tests to be legally marketed for sale. These tests typically simulate loading in a human body for a number of cycles equivalent to 10 years of use. Depending on the simulated loading condition, the number of test cycles may range from 1 to 400 million cycles. For example, stents that are intended to be used in the femoropopliteal arteries may be required to pass a bending test where the stent is bent to a radius of about 20 mm 1 to 10 million times or axially compressed about 10% 1 to 10 million times.

Although presently preferred embodiments of the present invention have been disclosed for illustrative purposes, those skilled in the art will appreciate that many additions, modifications, and substitutions are possible without departing from the scope and spirit of the invention as defined by the accompanying claims. For example, a stent could be made with only right-handed or only left-handed helical portions, or the helical strut band could have multiple reversals in winding direction rather than just one. Also, the helical strut band could have any number of turns per unit length or a variable pitch, and the strut bands and/or coil bands could be of unequal length along the stent.

What is claimed is:

1. A self expanding flexible stent comprising:
   a helical strut band helically wound about an axis of said stent, said helical strut band comprising a wave pattern of strut elements, said wave pattern having a plurality of peaks on either side of said wave pattern; and
   a plurality of coil elements helically wound about an axis of said stent, said coil elements progressing in the same direction as said helical strut band interconnecting at least some of said peaks of a first winding through or near to at least some of said peaks of a second winding of said helical strut band,
   wherein a geometric relationship triangle is constructed having a first side with a leg length $L_C$ being the effective length of said coil element between the interconnected peaks of said first and second winding of said helical strut band, a second side with a leg length being the circumferential distance between said peak of said first winding and said peak of said second winding interconnected by said coil element divided by the sine of an angle $A_s$ of said helical strut member from a longitudinal axis of said stent, a third side with a leg length being the longitudinal distance said helical strut band progresses in 1 circumference winding (Pl) minus the effective strut length $L_S$, a first angle of said first leg being 180 degrees minus said angle $A_s$, a second angle of said second leg being an angle $A_c$ of said coil element from said longitudinal axis and a third angle of said third leg being said angle $A_s$ minus said angle $A_c$,
   wherein a coil-strut ratio of a ratio of said first leg length $L_C$ to a length $L_S$ multiplied by the number of adjacent said wave pattern of said strut elements forming said helical strut band, $N_S$ is greater than or equal to about 1.

2. The stent of claim 1 wherein said helical strut band comprises:
   a plurality of said wave pattern of strut elements wherein strut elements of each of said wave patterns are connected to one another.

3. The stent of claim 2 comprising two said wave patterns.

4. The stent of claim 2 comprising three said wave patterns.

5. The stent of claim 1 further comprising:
   a strut portion connected to an end of said helical strut band, said strut portion wound about said axis of said stent and comprising a plurality of strut elements, said strut portion is wound about said axis of said stent with an acute angle formed between a plane perpendicular to said axis of said stent and said strut portion winding that is smaller than an acute angle formed between the plane perpendicular to said axis of said stent and the winding of said helical strut band; and transitional helical portions interconnected between said strut portion and a winding of said helical strut band adjacent said strut portion, said transitional helical band comprising transitional helical elements, said transitional helical elements connecting at least some of said coil elements of said winding of said helical strut band adjacent said strut portion and at least some of said strut elements of said strut portion.

6. The stent of claim 5 wherein adjacent ones of said transitional helical elements extending progressively at a shorter length around the circumference of said stent as the winding of said strut portion progresses away from said helical strut band.

7. The stent of claim 5 wherein some of said coil elements of said helical strut band are not connected to said strut portion.

8. The stent of claim 1 wherein each of said leg portions in said pair of leg portions have an equal length.

9. The stent of claim 1 wherein said coil elements include a curved transition at either end thereof, said curved transition portion connecting to said peaks of said helical strut member.

10. The stent of claim 1 wherein said coil elements comprise a pair of coil portions separated by a gap.

* * * * *